United States Patent [19]

Meiering et al.

[11] Patent Number: 5,204,262
[45] Date of Patent: Apr. 20, 1993

[54] ETHANOL SENSOR FOR COMPUTERIZED FERMENTATION CONTROL

[76] Inventors: Anton G. Meiering, 25 Hales Crescent, Guelph, Ontario N1G 1P4; Ronald E. Subden, 160 Maples Street, Guelph, Ontario N1G 2G7, both of Canada

[21] Appl. No.: 662,291

[22] Filed: Mar. 1, 1991

[30] Foreign Application Priority Data

Mar. 1, 1990 [CA] Canada .................................. 2001297

[51] Int. Cl.$^5$ ........................ C12M 1/34; C12M 1/04; G01N 25/18
[52] U.S. Cl. ..................................... 435/291; 422/98; 436/149; 435/313; 204/408; 204/415
[58] Field of Search ........................ 435/291, 807, 313; 422/83, 98, 68.1; 204/408, 415; 436/149; 364/497, 500

[56] References Cited

U.S. PATENT DOCUMENTS

| | | | |
|---|---|---|---|
| 3,955,929 | 5/1976 | Kawakami et al. | 436/133 |
| 4,404,284 | 9/1983 | Heider et al. | 435/291 |
| 4,569,826 | 2/1986 | Shiratori et al. | 422/98 |
| 4,656,140 | 4/1987 | Yamada et al. | 435/807 |
| 4,692,414 | 9/1987 | Yamada et al. | 435/291 |
| 4,706,493 | 11/1987 | Chang et al. | 422/98 |
| 4,849,180 | 7/1989 | Fukui | 422/98 |
| 4,869,873 | 9/1989 | Klein et al. | 422/93 |

OTHER PUBLICATIONS

Yamane, Application of Porous Teflon Tubing Method to Automatic Fed-Batch Culture of Microorganisms, Biotechnology and Bioengineering, vol. XXIII (1981) Parts I and II, pp. 2493-2524.

Primary Examiner—Robert J. Warden
Assistant Examiner—T. A. Trembley

[57] ABSTRACT

A probe for continuously measuring the precise concentration of liquid ethanol in a fermentation broth over the range of feasible fermentation temperatures. The probe includes a thermal sensor, a gas permeable membrane leading to a vapor channel, an ethanol vapor sensor in a vapor sensing chamber, and a microcomputer. The microcomputer is loaded with a first set of data defining the initial parameters of the fermentation broth and a set of data defining the ethanol diffusion rate through the gas permeable membrane as a function of the temperature of such fermentation broth. Inlet and outlet connection and tubular interconnections are provided for leading a flushing gas through the vapor channel, past the ethanol vapor sensor and out a vent outlet. Electrical lines leading from the thermal sensor to the microcomputer provide an input signal which is proportional to the temperature of the fermentation broth. Electrical lines also lead from the ethanol vapor sensor to the microcomputer to provide a signal which is proportional to the concentration of ethanol vapor. Evaluating software is loaded into the microcomputer to correlate the fermentation broth temperature, the ethanol vapor concentration and the ethanol diffusion rate through the gas permeable membrane as a function of temperature to provide an output of the actual concentration of liquid ethanol in the fermentation broth. On the basis of the ethanol liquid concentration so-determined, the microcomputer can automatically control temperature, pH, oxygen concentration and nutrient supply process parameters of the fermentation.

13 Claims, 1 Drawing Sheet

ETHANOL SENSOR FOR COMPUTERIZED FERMENTATION CONTROL

FIELD OF THE INVENTION

This invention relates to an apparatus for, and a method of, measuring the ethanol concentration in a fermentation broth on a continuous basis and provide data which indicates the need for corrections to environmental parameters of the broth.

DESCRIPTION OF THE PRIOR ART

U.S. Pat. No. 4,692,414 describes an apparatus for automatically controlling the feed rate of an alcohol solution in a process for producing vinegar by acetic acid fermentation using an automatic alcohol analyzer for measurement of alcohol concentration in a fermentation broth with a feeding apparatus for feeding alcohol solution as raw material to the fermenting broth, a control computer being coupled to the alcohol analyzer and to the feeding apparatus. The alcohol concentration in the fermenting broth is periodically measured by the automatic alcohol analyzer under direction from the control computer at given intervals which then controls the alcohol concentration in the fermenting broth at a desirable concentration by adjusting the feed rate.

U.S. Pat. No. 4,656,140 describes another method of measuring alcohol concentration of a acetic acid fermenting broth in which a tube made from material that is water-repellant and gas permeable is located inside the fermenter, the gas permeable tubing being connected to appropriate tubing through which a carrier gas flows at a predetermined rate, the carrier gas being fed to a semiconductive gas sensor after its passage through the gas permeable tube where the carrier gas picks up volatile components from the fermentation broth which have permeated through the tubing. These volatile components permeate through the gas permeable tubing in proportion to the concentration of each of those components in the fermenting broth. This patent mentions that, repeatedly, a correction for variation in temperature and pressure is necessary in order to accurately measure the alcohol concentration. To avoid this problem, U.S. Pat. No. 4,656,140 proposes another method where a portion of the fermenting broth is pumped by a pump to a heat exchanger where its temperature is adjusted to 40° C. and that portion then flows through a gas permeable tube. Carrier gas flows around the tube and then to a gas sensor. This arrangement avoids the corrections required for variation in the temperature and pressure but requires a pump and heat exchanger.

U.S. Pat. No. 3,955,929 mentions that it is already well known that metallic oxide semiconductors such as $SnO_2$, $ZnO$ or $Fe_2O_3$ have a property that, when it absorbs gases such as hydrogen, carbon monoxide or hydrocarbons, its electrical conductivity is increased. These gases are reducing gases. U.S. Pat. No. 4,569,826 illustrates one particular type of $SnO_2$ gas sensor for carbon monoxide or alcohol etc., in which, during measurement the gas sensitivity element is kept at a temperature of about 350° C. This sensor has a cylindrical substrate of insulating material with electrodes on the outer surface of the substrate which are covered with a gas sensitive body of $SnO_2$. In this particular sensor, the $SnO_2$ layer is covered with a catalyst. The resistivity measured between the electrodes provides an indication of the concentration of a gas such as ethanol around the sensor. A heater is provided in the central part of cylindrical substrate to maintain the sensor temperature at about 350° C.

U.S.Pat. No. 4,706,493 discloses another type of gas sensor for ethanol consisting of a semiconductor thin film composed of tin oxide having a palladium-gold catalyst on the exposed surface which, in operation, is kept at a temperature of about 250° C. by a polysilicon electrical resistance heating element.

SUMMARY OF THE INVENTION

Objects of the present invention are to provide an improved apparatus for, and a method of, measuring the ethanol concentration in a fermentation broth in a continuous and accurate manner.

In accordance with these objects and in accordance with one embodiment of the invention, an apparatus for determining the concentration of ethanol in a fermentation broth consists of a probe having a slim cylindrical elongated stem with an enlarged housing located at the top of the stem, the housing containing a printed circuit board and a semiconductive ethanol sensor, the stem having a recessed side portion near its bottom in which a gas permeable tube is located so that the outer surface of the stem extends outwardly beyond the outer surface of the gas permeable tube, the bottom of the stem being sealed by a wall with a temperature sensor being located at said bottom, leads from the temperature sensor extending upward inside the stem to the printed circuit board in said housing which contains a gas flow inlet connected to an inner tube that extends downward inside the stem and is connected to an inlet of the gas permeable tube whose outlet is connected to an inlet of the ethanol sensor, leads from the ethanol sensor being connected to the printed circuit board, the printed circuit board being connected to an electrical outlet in the housing for connection to a microcomputer.

In a further embodiment of the invention, the wall sealing the bottom of the stem is recessed from the bottom edge of the stem forming a cavity in which the temperature sensor is located.

Therefore, to the accomplishments of the foregoing objects, the invention consists of the foregoing features hereinafter fully described and particularly pointed out in the claims, the accompanying drawing and the following disclosure describing in detail the invention, such drawing and disclosure illustrating but one of the various ways in which the invention may be practiced.

DESCRIPTION OF THE PREFERRED EMBODIMENT

Figure 1:
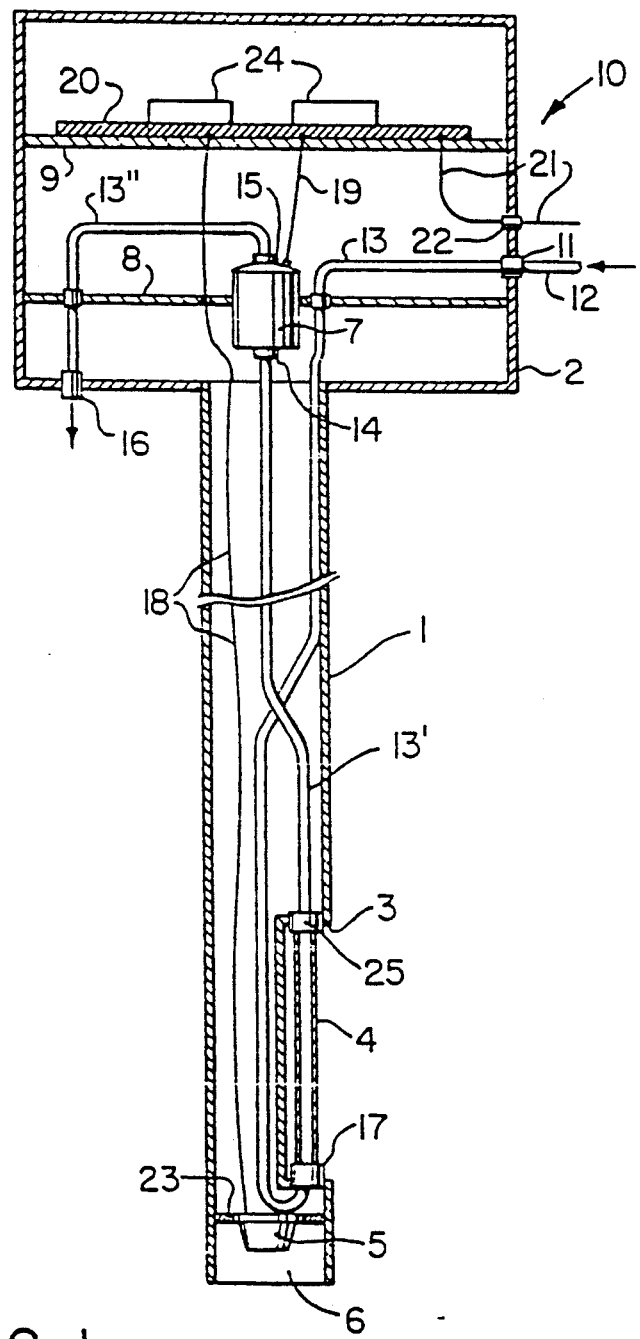
FIG. 1 is a partial cross-sectional view of a probe according to the present invention.

FIG. 1 illustrates a probe according to a preferred embodiment of the invention. The sensor 10 consists of a long slim tubular stem 1 with an enlarged upper cylindrical housing 2 forming a single integrated probe. The stem 1 is intended to be inserted into a fermentation broth so that the apparatus can determine the ethanol concentration in that broth. The lower end of tubular portion 1 is open with a wall 23 located a short distance above the lower end sealing the remaining inner portion of tubular stem 1 from contact with the fermentation broth. The wall 23 and open lower end of the stem form a cavity 6 in which a thermal sensor 5 is located. Thermal sensor 5 may be an active thermal transducer or a thermocouple. The lower end of stem 1 extends below the thermal sensor 5 and provides protection for thermal sensor 5 from mechanical damage while allowing thermal sensor 5 to be in contact with the fermentation broth. A slot in the wall of the stem extending up to a wall 23 avoids getting an air bubble trapped in the cavity.

Leads 18 from thermal sensor 5 extends upward inside the hollow stem 1 to integrated circuits 24 on printed circuit board 20 located in an upper portion of cylindrical housing 2. Spacers 9 hold circuit board 20 in its proper position in housing 2, the circuit board being readily accessed by removing a cap at the top of housing 2. The cap is not shown in the Figure. That cap completely seals the inner portions of housing 2 and stem 1 against the entrance of dust, moisture and gases.

An elongated recessed portion 3 in the lower side of tubular stem 1 forms a protective cutaway for a water-repellant and gas permeable tubing 4. Tubing 4 is positioned inside the recessed portion 3 between an outlet connection 25 at the top edge of recessed portion 3 and an inlet connection 17 at the bottom edge of recessed portion 3. The outer surface of the stem 1 extends outwardly beyond the outer surfaces of gas permeable tube 4 which provides some protection for the tube from mechanical damage. The recessed portion 3 is located in the lower portion of stem 1 so that tubing 4 is near the thermal sensor 5. The thermal sensor 5, as a result, measures the temperature of the fermentation broth which is in the immediate vicinity of gas permeable tube 4.

An inlet gas flow for sensor 10, such as a medical air supply fed through a precision control valve, is connected to an inlet 11 in housing 2 via tube 12. The inlet connection 11 is attached to small copper tubing 13 which extends downward inside of stem 1 to its lower portion where tubing 13 is connected to the inlet connection 17 for tube 4. The outlet connection 25 for tube 4 is connected to the inlet 14 of a semiconductor ethanol sensor 7 by tubing 13', outlet 15 being connected to an exhaust outlet 16 in housing 2 by tubing 13". The $SnO_2$ ethanol sensor 7 is held in position inside of housing 2 by supports 8. The supports 8 holds the ethanol sensor 7 so that it is spaced away from circuit board 20 to which it is electrically connected by a number of leads 19. The printed circuit covers only a portion of the top of housing 2 with the ethanol sensor being located in a portion of housing 2 which is directly below the printed circuit board. A couple of leads 19 supply power for a heater in sensor 7 and further leads supply information from the sensor 7 to integrated circuits 24 on circuit board 20. These integrated circuits 24 provide information regarding the temperatures of the fermentation broth and the ethanol concentration reading determined by sensor 7 to a microcomputer interface via leads 21 through an electrical outlet 22 in housing 2. The amount of ethanol diffusing through tube 4 is dependent on the temperature of the fermentation broth. Therefore, the ethanol concentration reading as determined by sensor 7 is not accurately an indication of the actual ethanol concentration in the fermentation broth.

The microcomputer is provided with a set of data about the initial concentration of components such as acids, cellulosic components as well as ethanol, density and microbial concentration. That microcomputer also contains software and data regarding the ethanol diffusion rate though the gas permeable tube 4 as function of temperature of the fermentation broth along with specific programs describing the sensor as well as fermentation dynamics. From these and along with readings from thermal sensor 5 and ethanol sensor 7, the microcomputer can determine the actual ethanol concentration in the fermentation broth in an accurate and continuous manner. Fermentation data can then be determined and continuously displayed or printed by the microcomputer in tabulated or graphical form and warnings can be issued in time to indicate the need for corrections to environmental parameters. That information can be used for automatic control of temperature, pH, oxygen, concentration, nutrient supply and other important process parameters. This is in contrast to conventional methods wherein manually controlled equipment can cause critical delays in response time. This sensor 10 in combination with software in a dedicated control computer allows an adaptive and interactive control of the fermentation process.

Tube 4 may consist of a silicone, TEFLON ® or nitrate cellulose membrane. In one particular sensor, a silicone membrane 4 was used with a Taguchi TGS #812 sensor of the Figaro Engineering CO. of Japan. The heating coil for this particular sensor was maintained at a constant 400° C. during operation. The gas permeable silicone membrane was positioned in a protective cutaway at the lower end of a 600 mm long stainless steel sensor stem 1 having a 25 mm diameter. Standard ⅛' copper tubing transports carrier gas to the straight 0.3175 mm (⅛") diameter silicone membrane which has a wall thickness of 0.79375 mm (1/32") and a total length of 80 mm. Medical air during operation was fed from precision control valve to the sensor at a flow rate of 7.5 $ml$/min.

That sensor can be mounted in a quick coupling device in a fermenter wall or attached to a float which allows stem immersion to a standard depth from the liquid surface in the fermenter. The stainless steel stem and housing are sealed against volatiles, foam and liquids. An impermeable flexible tubing needs to be used for the carrier gas supply such as TEFLON ® tubing, when the sensor is floating.

Therefore, while the present invention has been shown and described herein in what is believed to be the most practical and preferred embodiment, it is recognized that departures can be made therefrom within the scope of the invention, which embodiment is therefore not to be limited to the details disclosed herein but is to be accorded the full scope of the claims so as to embrace any and all equivalent apparatus.

We claim:

1. A probe for continuously measuring the precise concentration of liquid ethanol in a fermentation broth over the range of feasible fermentation temperatures, said probe comprising:
   a. a thermal sensor;
   b. a gas permeable membrane leading to a vapor channel;
   c. an ethanol vapor sensor in a vapor sensing chamber;
   d. a microcomputer, said microcomputer being loaded with a first set of data defining the initial concentration of fermentation broth, acid and cellulosic components and microbial concentration, and density, and a second set of data defining the ethanol diffusion rate through said gas permeable membrane as a function of the temperature of said fermentation broth;

e. inlet means for a flushing gas and outlet means for said flushing gas and tubular interconnections for said flushing gas, said tubular interconnections being provided for leading said flushing gas through said vapor channel, through said vapor sensing chamber, past said ethanol vapor sensor, and out through said outlet means;

f. electrical lines leading from said thermal sensor to said microcomputer, said electrical lines being constructed to carry an output signal which is proportional to the temperature of said fermentation broth;

g. electrical lines leading from said ethanol vapor sensor to said microcomputer, said electrical lines being constructed to carry an output signal which is proportional to the concentration of ethanol vapor; and h. evaluating software loaded into said microcomputer to correlate said output signal proportional to said fermentation broth temperature, said output signal proportional to said ethanol vapor concentration and said second set of data defining said ethanol diffusion rate through said gas permeable membrane as a function of temperature and to provide a single output consisting of the actual concentration of liquid ethanol in said fermentation broth.

2. A probe as defined in claim 1 including means in said microcomputer for, on the basis of said ethanol liquid concentration so-determined, automatically controlling temperature, pH, oxygen concentration and nutrient supply process parameters.

3. A probe as defined in claim 2 further including a housing portion accommodating said microcomputer, said ethanol sensor, and said inlet means and outlet means for said flushing gas, and a depending stem portion accommodating said thermal sensor and said gas permeable membrane.

4. A probe as defined in claim 3 including a heating coil adjacent to said temperature sensor and operative to maintain the temperature of said thermal sensor at a predetermined thermal.

5. A probe as defined in claim 3 wherein said housing portion and said depending stem portion are each made of stainless steel.

6. A probe as defined in claim 1 wherein said thermal sensor is a thermal transducer.

7. A probe as defined in claim 1 wherein said thermal sensor is a thermocouple.

8. A probe as defined in claim 1 wherein said ethanol sensor is an $SnO_2$ ethanol sensor.

9. A probe as defined in claim 1 wherein said gas permeable membrane comprises a tube at least a portion of which is formed of a material selected from the group consisting of a silicone, a polytetrafluoroethylene polymer and cellulose nitrate membrane.

10. A method for continuously measuring the precise concentration of liquid ethanol in a fermentation broth over the range of feasible fermentation temperatures, said method comprising the steps of:

a. contacting a fermentation broth with a thermal sensor, thereby continuously to measure the temperature of said fermentation broth, said thermal sensor thereby providing an electrical output signal which is proportional to the temperature of said fermentation broth;

b. contacting said fermentation broth with a gas permeable membrane, thereby to permit ethanol in said fermentation broth to diffuse, in the form of ethanol vapor, across said gas permeable membrane into an ethanol vapor zone;

c. flushing said ethanol vapor zone with a gas, said gas passing from a gas inlet zone into said ethanol vapor zone, then through a sensor zone in contact with an ethanol sensor, and from said sensor zone through an outlet zone to be vented;

d. determining the concentration of ethanol vapor in said sensor zone by means of said ethanol sensor, said ethanol sensor thereby providing an electrical output signal which is proportional to said concentration of ethanol vapor;

e. providing a microcomputer loaded with a first set of data defining the initial concentration of fermentation broth, acid and cellulosic component and microbial concentration, and density, and a second set of data defining the ethanol diffusion rate through said gas permeable membrane as a function of the temperature of such fermentation broth;

f. entering said electrical output signal proportional to said temperature of said fermentation broth, and entering said electrical output signal proportional to said concentration of ethanol vapor as inputs to said microcomputer; and g. correlating said data by means of evaluating software to correlate said fermentation broth temperature, said ethanol vapor concentration and said ethanol diffusion rate through said gas permeable membrane as a function of temperature to provide an output value consisting of the actual concentration of liquid ethanol in said fermentation broth.

11. A method as defined in claim 10 including the additional step of, on the basis of said ethanol liquid concentration so-determined, automatically controlling temperature, pH, oxygen concentration and nutrient supply process parameters.

12. A method as defined in claim 10 wherein said flushing gas is provided by a medical air supply.

13. A method as defined in claim 10 including the step of maintaining the temperature of said temperature sensor at a constant temperature of 400° C.

* * * * *

UNITED STATES PATENT AND TRADEMARK OFFICE
CERTIFICATE OF CORRECTION

PATENT NO. : 5,204,262
DATED : April 20, 1993
INVENTOR(S) : Meiering et al.

It is certified that error appears in the above-identified patent and that said Letters Patent is hereby corrected as shown below:

On the title page, item (30) below "Foreign Application Priority Data" delete "2001297" and insert therefor -- 2011297 --

On col. 5, line 42 delete "temperature" and insert therefor -- thermal --.

On Col. 5, line 44 delete "thermal" and insert therefor -- temperature --.

Signed and Sealed this

Twenty-eighth Day of December, 1993

Attest:

BRUCE LEHMAN

Attesting Officer

Commissioner of Patents and Trademarks